United States Patent [19]

Leary et al.

[11] Patent Number: 5,204,884
[45] Date of Patent: Apr. 20, 1993

[54] SYSTEM FOR HIGH-SPEED MEASUREMENT AND SORTING OF PARTICLES

[75] Inventors: James F. Leary; Mark A. Corio; Scott R. McLaughlin, all of Rochester, N.Y.

[73] Assignee: University of Rochester, Rochester, N.Y.

[21] Appl. No.: 671,009

[22] Filed: Mar. 18, 1991

[51] Int. Cl.$^5$ .............................................. G01N 27/00
[52] U.S. Cl. .......................................... 377/10; 377/12
[58] Field of Search ..................................... 377/10, 12

[56] References Cited

U.S. PATENT DOCUMENTS

| | | | |
|---|---|---|---|
| 4,086,631 | 4/1978 | Vick | 377/10 |
| 4,115,806 | 9/1978 | Morton | 377/10 |
| 4,653,078 | 3/1987 | Aritomi et al. | 377/10 |

Primary Examiner—William L. Sikes
Assistant Examiner—Scott A. Ouellette
Attorney, Agent, or Firm—Cooper & Dunham

[57] ABSTRACT

A system for sorting particles is arranged such that the presence or absence of multiple parameters is determined for each particle in a flow of particles, and a logic condition is determined based on the multiple parameters. Thereafter, particles are outputted from the system when the logic condition is present. Accordingly, multiparameter high-speed measurements of a rare subpopulation of particles (e.g. biological cells) can be made amidst a larger population of particles with differing characteristics. When attached to a multiparameter flow cytometer/cell sorter and microcomputer, the system allows multiparameter analysis of cells at rates in excess of 100,000 cells/sec. This system can be an outboard module attached to a commercially available or home-built flow cytometer.

22 Claims, 8 Drawing Sheets

SYSTEM FOR HIGH-SPEED MEASUREMENT AND SORTING OF PARTICLES

The invention was made with government support under grant number R01-GM386645 from the National Institute of General Medical Sciences and grant number R01-HD20601 from the National Institute of Child Health and Development.

BACKGROUND AND SUMMARY OF THE INVENTION

This invention relates to a system for investigating particles, and in particular to such a system wherein a plurality of detection signals from a particle or cell having pre-determined parameters can be characterized at very high signal processing rates.

The concentration and biological activity of cells can be investigated by observing a spectrum of light modulated by the cells. In one method of spectral analysis of cells, substances can be investigated which show characteristic peaks, or maxima, of absorption when the light absorption is plotted as a function of light wavelength. In another method, fluorescence is used to investigate cells. In this method, cells are analyzed by their capacity to absorb light at a given wavelength and emit at a longer wavelength, a property which is known as fluorescence.

Systems for sorting cells which automate the abovedescribed methods may be referred to as flow cytometer sorting systems. These systems are used in the medical research and diagnostic fields for the rapid analysis and processing of biological cells. Systems for sorting particles suspended in a liquid according to certain characteristics are discussed in U.S. Pat. No. 3,393,606, 4,063,284 and 4,487,320. Specifically, in these prior art systems optical measurements of characteristics of each particle of a group of particles are made while the particles are suspended in a liquid. In one such system, a flow cytometer cell sorter analyzes cells or particles in suspension which are stained with a fluorescent dye and are carried single file in a fast-moving liquid stream sequentially through a tightly focused laser beams whose wavelength is adjusted to excite the fluorescent dye. The fluorescence and/or light scatter produced during the laser beam crossing is collected by an optical system and projected through spectral filters onto photodetectors. These detectors convert the fluorescence and/or scattered light to electrical pulses whose amplitudes depend on the total light reaching the detectors. Particles having predetermined characteristics are recognized by their distinctive fluorescence and/or scattered light intensities. After measurements of the characteristics, each particle flows in a liquid jet stream until the particle reaches a point where the jet breaks into discrete droplets. At this point, an electric charge is induced on each droplet containing a particle to be sorted and the charged and uncharged droplets are then sorted electrostatically.

Analysis and isolation of certain subsets of cells of interest on the basis of certain predetermined characteristics are of interest to researchers and clinicians in many areas of biology and medicine, including detection of somatic cell mutations in mutagenized cells (Jensen et al., Determination of somatic mutations in human erythrocytes by flow cytometry. Prog Clin Biol Res 209B: 177-184, 1986), detection of human fetal cells in maternal blood for prenatal diagnosis of birth defects (Cupp et al., Rare-event analysis methods for detection of fetal red blood cells in maternal blood. Cytometry 5; 138-144, 1984), detection of CALLA+ cells (Ryan et al., Improved detection of rare CALLA-positive cells in peripheral blood using multi-parameter flow cytometry. J Immunol Methods 74(1): 115-275, 1986, 1984), and detection of minimal residual diseases (Visser et al., Detection of minimal residual disease in acute leukemia by flow cytometry. Ann NY Acad Sci 468: 268-275, 1986). The subsets of cells of interest often occur at very low frequencies, i.e. $10^{-5} - 10^{-7}$ of the cells sampled are of interest. In the above-described prior art flow cytometer systems analysis of a subset of cells of interest requires analysis of all the cells in the sample whether or not they are part of the subset of interest. The analysis is performed by digitizing and storing detection signals from all cells. In the above-described flow cytometers, which have operating rates at below 10,000 cells/sec, many hours are required to analyze and/or isolate the cell subpopulations of interest and sufficient storage resources are needed to store information from all analyzed cells. This required amount of time for analysis and the storage requirement for digitized cells is unsuitable for many studies.

For these and other reasons, proposals have been made in the past for faster cell processing speeds in the analysis of cell subpopulations of interest or rare subpopulations. For example, systems have been proposed which operate at rates of 15,000-25,000 cells/sec (Peters et al.,: The LLNL high-speed sorter: design features, operational characteristics, and biological utility. Cytometry 6: 290-301, 1985). This system increases the cell processing speed by increasing the pressure in the jet stream to increase the droplet production frequency. However, while this system achieves faster cell processing rates, the system is similar to the original flow cytometric sorting systems in that detection signals from all cells are digitized and the information is stored as either correlated or uncorrelated data of all signals from all cells.

The invention makes use of a recognition that for rare cell subpopulations most of the cells are not of interest. In the invention all cells are classified as either "possibly of interest" or "not of interest" in the invention circuitry without storage by an acquisition system. The invention also makes use of the classification of a cell by multiple parameters which are determined by a plurality of detectors. A cell is determined to be "possibly of interest" from multiple parameters, unlike prior art systems which determine a cell from only a single parameter which may not be able to discriminate reliably between true positive rare cells and false-positive cells in the total population of the cells.

Additional advantages of the present invention over prior art systems are that, the use of the invention in combination with commercially available cytometers allows the flow cytometers to operate at rates of more than 100,000 cells/second. Further, the invention reduces the problems of storing and analyzing data sets containing $10^7 - 10^9$ cells by storing only data of interest or data about which an experimenter cannot be certain as to whether it must stored for further analysis. Therefore, data classified by the system as "not of interest" can be counted but not digitized and/or stored.

In an exemplary and nonlimiting embodiment of the invention, high-speed analog comparators and signal gating circuitries accept incoming analog detection signals, for example from commercially available particle detectors, in the range of from about noise level to about 1.0 volt. The signals from the particle detectors may represent different characteristics, for example, such as those reflected in total signals, doublet information, rare signals or other input signals. For example, one of these signals might represent perpendicular light scatter (PLS), and the others might represent one or more colors of fluorescence e.g. (RARE1, RARE2, RARE3). The total signal (TOTAL) represents a signal which is present for all cells which are passed through the system. In operation of the system, a TOTAL signal above a user determined threshold reference value triggers the initiation of the system.

After analog pre-processing to properly condition and buffer the incoming detection analog signals, each analog detection signal is split into two paths. In the first path, the detection signals are applied to high speed differential comparators. In the second path, the detection signals are applied to a plurality of signal gates which are controlled by a gate logic signal.

In this embodiment, each of the comparators receives a different level reference threshold voltage. When the detections signal is greater than the reference voltage, a compared pulse is generated by the comparator.

The compared pulses are sent to counter circuitry for counting the compared pulses to measure the total number of cells producing respective detection signals. The compared pulses which originate from rare signals and the compared pulses which originate from the total signal are sent to gating logic circuitry. The gating logic circuitry produces a gate control signal to control the analog outputs of the system as a user-selectable function of the rare signals, hereafter called the gate logic condition. In response to a gate logic condition, which means that a "rare cell" has been detected, signals of the second path which were received at the signal gates are gated to subsequent hardware, for example a data acquisition system or a flow cytometer, for further processing.

In the embodiment described above, it has been discovered that some detection signals which contribute to the gate logic condition may be slightly delayed with respect to each other. One practical example of where this can occur is the sorting of a desired property (e.g. presence of a cell's nucleus) which will be detected in the particle detectors within some time period (i.e. period defined by some physical property such as the positions of the membrane edges of a biological cell and its nucleus). Accordingly, the system is adapted to respond to all detection signals (or lack thereof) within a specified time interval. In an exemplary implementation of the invention, the values of all signals and their logic condition are determined within a period of approximately 2 microseconds.

In this implementation, the signals in the second path are delayed for a time period corresponding to a defined timed window to produce delayed analog signals. In response to a logic condition being determined within the defined time window, which indicate that these signals come from a "rare cell," the analog signals are gated to subsequent hardware. In a second alternate implementation, a second detection system is used to obtain the prior knowledge of all detection signals. In this second implementation, all signals of the first path are compared with respective thresholds to identify rare signals and total signals, as described above. This part of the second implementation is similar to the first implementation. However, in this second implementation, the second path of signals, which are in fact the same as the detection signals applied to the comparators, are generated from a second detection system. Therefore, in this implementation a delay line is not required.

In a second exemplary embodiment of the invention, a doublet threshold reference voltage is provided to determine information on doublets, and to determine the threshold setting of the total signal and theoretically model coincidence or missed events. A doublet is a condition where pulses from two nearby cells occur sufficiently close in time such that the signal pulses of the two nearby cells overlap. The doublet threshold is set at a second threshold value which is chosen to be higher than the threshold for the total signal. This doublet threshold is sent to a doublet reference comparator. The total signal is also sent to the doublet comparator and the comparator compares the total signal to the doublet threshold. Thereafter, when the total signal is greater than the doublet threshold a compared pulse is generated and applied to a doublet counter. Therefore, the use of a doublet threshold can determine when a doublet event occurs in the total signal which allows the system to count two cells rather than a single overlapping pulse which would be determined from the measurement of only a total reference threshold. Additionally, the doublet threshold can be used to determine what the value of the total threshold reference signal should be to accurately count all cells. Moreover, mathematical relationships can be used between the counts of cells gated through the system in a predetermined time window and counts of cells compared to doublet thresholds to optimally set the first total threshold for measuring all cells.

DETAILED DESCRIPTION

Figure 1:
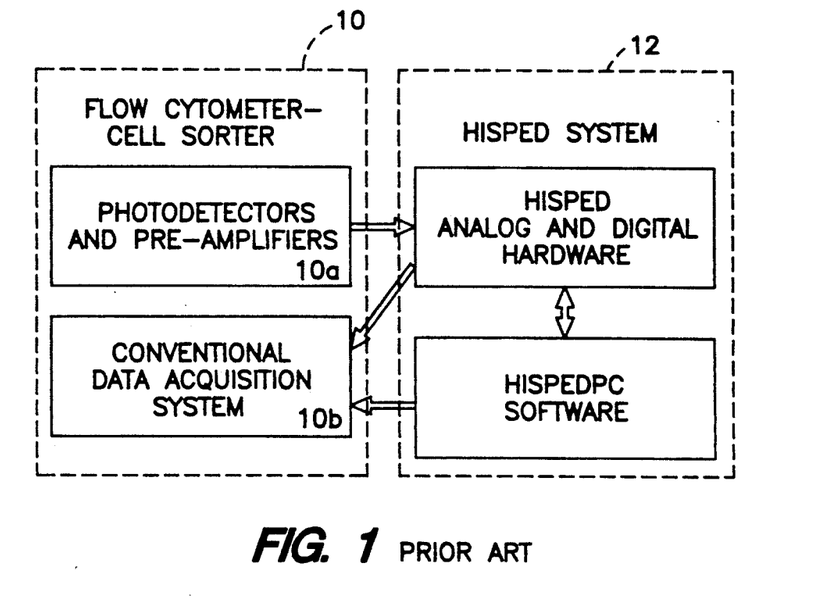
FIG. 1 is a block diagram of an embodiment of the invention particle sorting system, working with a prior art flow cytometer/cell sorter system.

FIG. 1 illustrates a particle characterization system 12 in accordance with the present invention, used with a prior art flow cytometer cell sorter 10. System 12 receives input signals from photodetectors and preamplifiers 10a, processes these signals by analog and digital hardware and passes the processed data to a prior art data acquisition system 10b.

Figure 2:
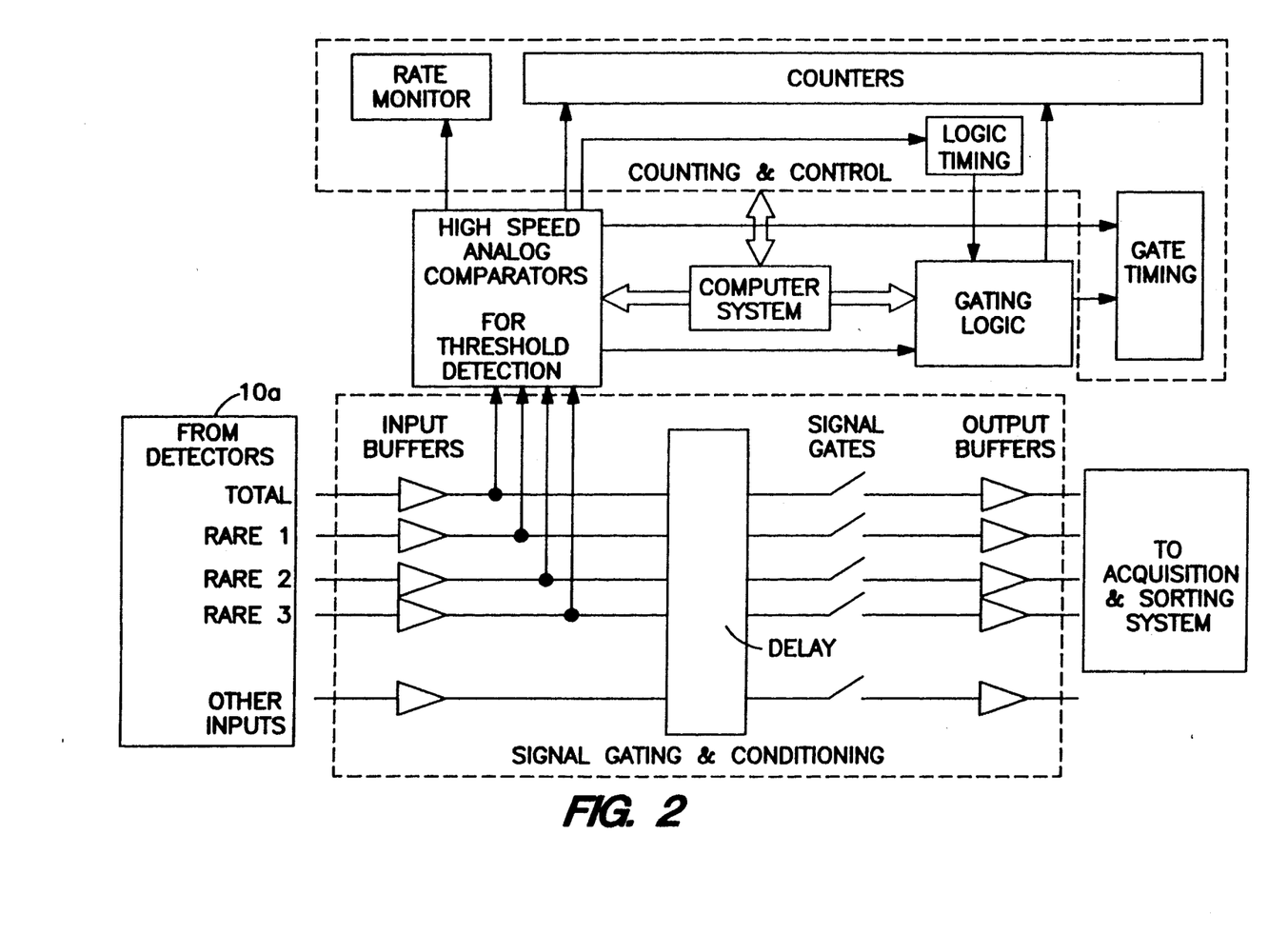
FIG. 2 is a block diagram of a particle sorting system according to an embodiment of the invention.
Figure 3A:
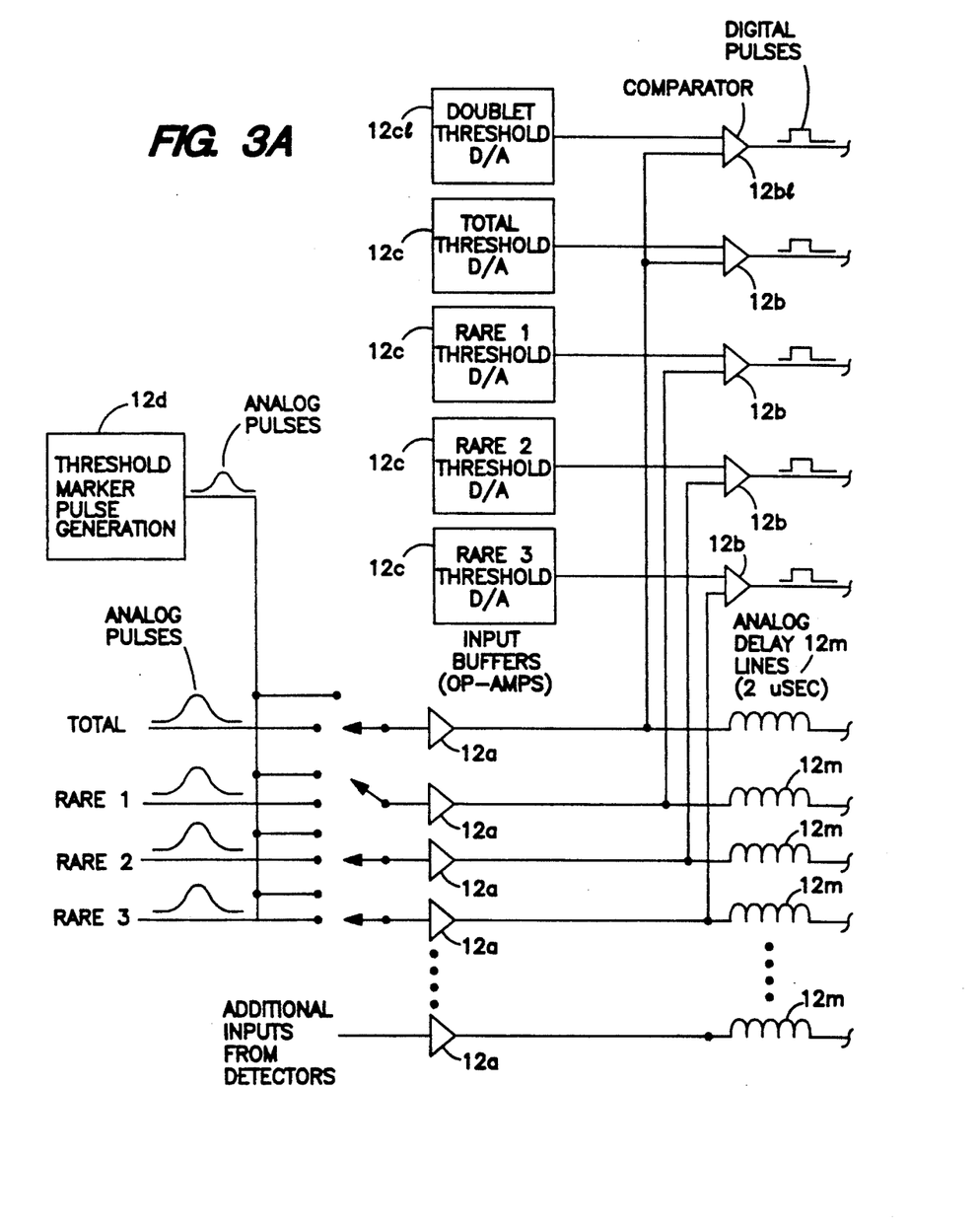
FIGS. 3A and 3B are logic diagrams of electrical circuitry for a particle sorting according to an embodiment of the invention.
Figure 3B:
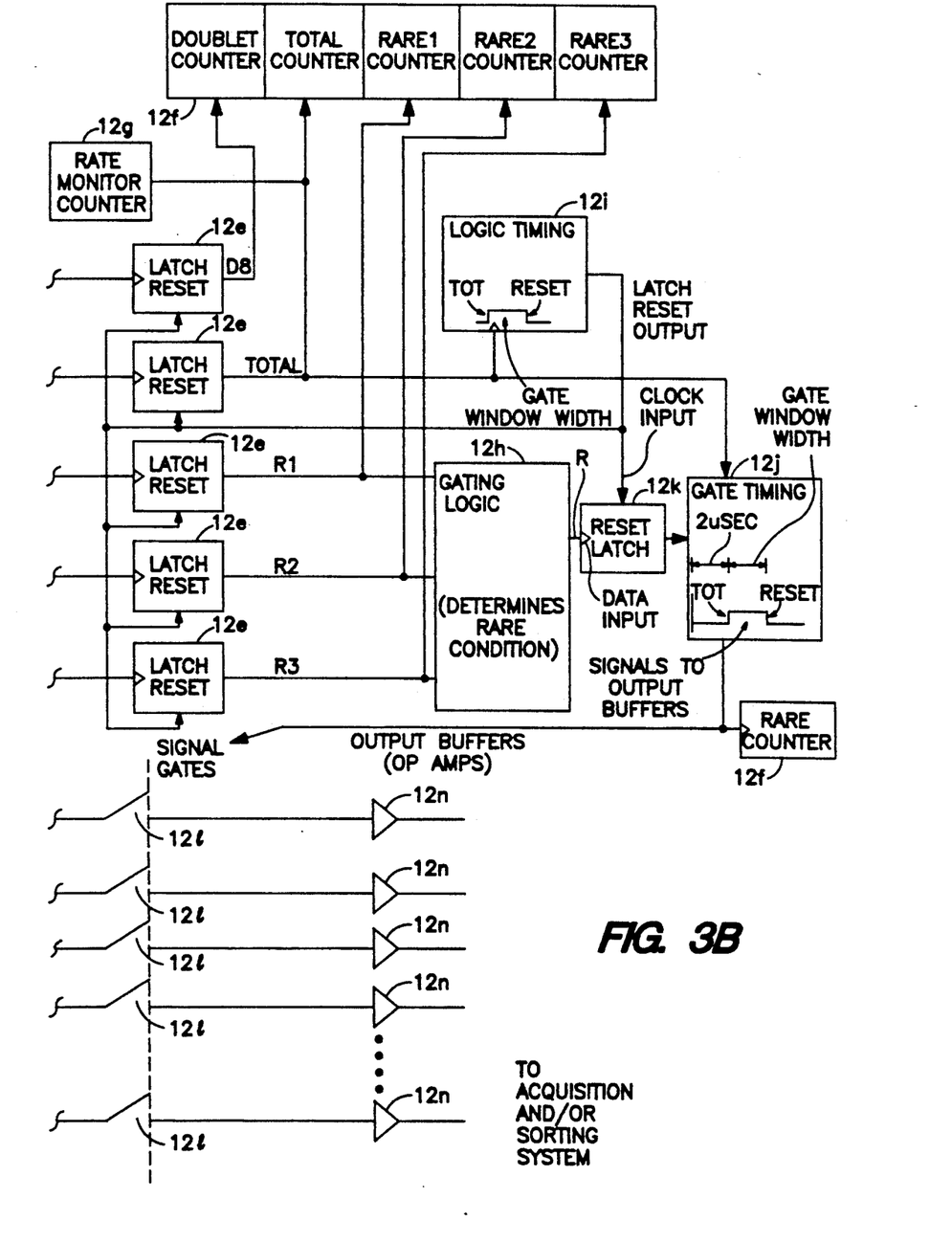

FIGS. 2, 3A and 3B illustrate a preferred embodiment of a system constructed in accordance with the present invention. The system receives detection signals from particle detectors 10a, such as total signals, rare signals or other input signals. The incoming detected analog signals from the detectors are in the range of from about noise level to about 1.0 volt. For example, one of these signals might represent perpendicular light scatter (PLS), and the others represent one or more colors of fluorescence (RARE1, RARE2, RARE3). The total signal (TOTAL) represents a signal generated when any cell passes through the system. In this embodiment, input buffers, such as operational amplifiers 12a, are provided to receive the detection signals and to properly condition or amplify the incoming detection signals.

The signals issuing from input buffers 12a go to respective comparators 12b each of Which determines if the received signal has crossed a threshold reference voltage. The threshold voltages come from respective threshold sources 12c whose voltage levels are setable by the user of the system.

A threshold marker-pulse generation unit 12d is used to overcome difficulties arising in setting the threshold reference values from sources 12c because the signal paths from the invention to subsequent prior art acquisition systems 10b can vary in gain and/or can be nonlinear (e.g. they can pass through log amplifiers, integrating amplifiers or amplifiers which are not truly linear in the relevant range). During initiation of the system, appropriate threshold settings for rare input signals are determined using the threshold marker generator 12d. These settings may be determined by acquiring data in data acquisition system 10b, that has been gated through the system from threshold marker generator 12d with logic conditions set to receive all rare signals. The acquired data can be measured using histograms or bivariate displays to determine threshold reference values for sources 12c.

To compensate for the lack of knowledge of the transfer function of each detector signal path, the systems send pulses to input buffers 12a, from threshold marker generator 12d instead of detector signals from detectors 10a. In this case, threshold marker generator 12d sends pulses equal in amplitude to an estimated threshold value for each particular detector input. The pulses are sent into the system with the logic gate condition set to "rare". Therefore, all signals will be passed to data acquisition system 10b. Data acquisition system 10b observes an input (e.g single channel peak on histogram display) indicating the position of the threshold from each respective source 12c. The threshold reference voltage setting on the system may then be appropriately adjusted up or down to position the respective threshold of each source 12c as determined from the data acquisition system's display.

This type of threshold initiation allows for accurate positioning of the threshold reference voltages for each of the rare input signals without the need to characterize the amplification path's gain profile for each signal, since the gain profile could change with any adjustments to the amplifiers being used. Even if the amplification path's gain profile were known and constant, this invention would still eliminate the need for conversion calculations to determine the system's threshold values for sources 12c from values obtained from acquisition system 10b.

When the signal received at a comparator 12b has crossed the reference voltage, a compared pulse signal is generated by the comparator. Connected to comparators 12b through latches 12e are respective counters 12f in which the compared pulses obtained from each of comparators 12b are applied to a respective digital counter 12f. Counters 12f are comprised of 32 bit counters for the compared pulses of the detected total and doublet signals and 24 bit counters for the compared pulses of the detected rare signals. Compared pulses from the comparator 12b for the total signal are also applied to a rate monitor counter 12g for determining the rate at which the signals are being applied to the system from the detectors.

The compared pulse signals are also applied to a gating logic mechanism 12h for determining a multiparameter rare condition which is the logic gate condition. The logic gate condition is set by the user to be any Boolean combination of the compared rare signals, including lack of a given rare signal. Gating logic mechanism 12h receives the compared pulses of the rare signals and logically determines if the compared pulses received satisfy the multi-parameter rare condition. Gating logic mechanism 12h is controlled by a logic timing circuit 12i for determining a window size or length of time for receiving compared pulses from the compared rare input signals, i.e. 2 microseconds.

Figure 4:
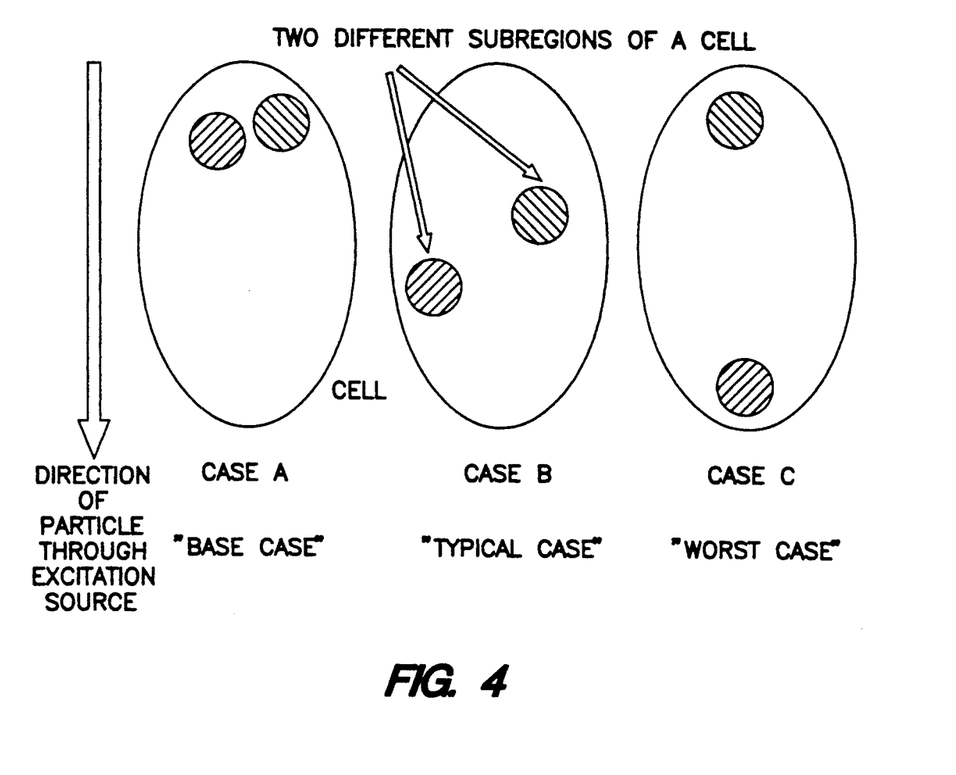
FIG. 4 is an illustration useful in explaining timing of measurements of rare cell signals.

As illustrated in FIG. 4, the multiple parameters from particle detectors 10a may occur at different times. For example, if two nuclei are present in a cell, the first nucleus may be detected earlier in time than the second nucleus. Logic timing circuit 12i receives a compared pulse of the total signal and generates a predetermined time window during which the compared pulses of the rare signals required for the rare condition must be received by gate logic mechanism 12h. After the predetermined length of time has expired, logic timing circuit 12i applies an "end of window" control signal or a reset signal to latches 12e. Thereafter, latches 12e are reset to receive compared pulses and determine a rare condition for a new set of rare signals during a subsequent time window. Gating logic mechanism 12h is adapted to form a gate control signal "R" which represents the gating logic mechanism's 12h determination of a rare condition within the time window. A rare condition is determined by comparing pulse signals to a Boolean condition.

The gate control signal R is supplied via a latch to gate timing circuit 12j for controlling a plurality of signal gates 12l. Gate timing circuit 12j receives the total signal, delays the signal by the predetermined delay which is the time needed to open the gates, and adds the time window (e.g. 2 $\mu$sec) to the pre-determined delay. Therefore, if gate timing circuit 12j receives a gate control signal from logic mechanism 12h within a 2 $\mu$sec delay the gate timing circuit 12j will pass the gate control signal to signal gates 12l. Signal gates 12l open in response to receiving the gate control signal. During the operation of the gate logic mechanism 12h, signal gates 12l receive detection signals which have been delayed in time with analog delay line coils 12m. On receipt of gate control signal R delayed detection signals are passed from signal gate 12l to an output of system 12.

Latches 12e are connected to the comparators and operate such that when a compared pulse is received the signal is latched. Specifically, each latch 12e has two inputs, a data input and a clock input, and one Q output. On the rising edge of a clock input from the logic timing circuit the data that is in the data input is latched and outputted to the Q output. Therefore, the Q output will only change on the rising edge of the clock input and will output whatever data is present in the data input at that time. In this implementation, the data input of the latches is tied to a high state such that whenever a rising edge of a clock signal is received, the output will be high state or "1". The latch will remain in a high state until receiving a reset signal at which time the output will be forced to a low state or "0". A latch $12k$ is also provided at the output of the gating logic mechanism $12h$ which is controlled by the logic timing circuit $12i$ such that once the gate window width is exceeded a gate control signal R is latched. In this implementation, logic timing circuit $12i$ transmits a latch reset output signal to latches $12e$ connected to the comparators at the end of the gate window. Therefore, whether or not a rare condition is determined within the time window, a latch reset signal is supplied from the logic timing $12i$ at the end of the gate window to latches $12e$ and latch $12k$. A clock signal latches the rare condition to be used for gate output so that more inputs may be interrogated.

Output from signal gates $12l$ is connected to output buffers $12n$, i.e. operational amplifiers, for transmission to data acquisition $10b$ and/or sorting system. Nonlimiting examples of data acquisition systems $10b$ are systems with analog to digital converters such that the system digitizes peak heights of the analog detection signals, integrals of height under the analog signal or widths of the analog signal. The digitized signals of the data acquisition system $10b$ can be transmitted to a computer such as a PDP-11/73 miorocomputer (not shown) for storage and further analysis.

Figure 5:
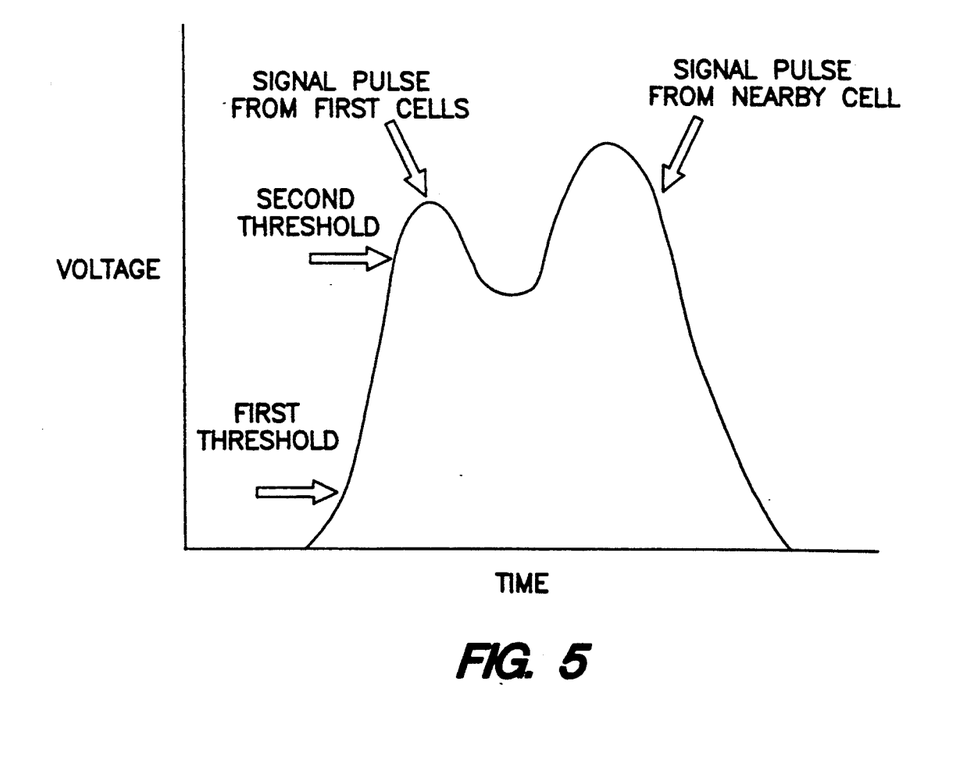
FIG. 5 is an illustration of signal pulses of a first and second nearby cell and first and second threshold values.

Referring to FIGS. 3A and 3B, in this embodiment of the invention a doublet threshold reference source $12cl$ provides a signal to a doublet comparator $12bl$. During the initiation and operation of the system, the use of the doublet comparator $12bl$ determines a "coincidence" condition, which exists if detected particles are sufficiently close such that the first threshold or total threshold incorrectly measures the overlap of two TOTAL signal pulses from two cells as a single cell. FIG. 5 illustrates an example of signal pulses from first cells and nearby cells. In the initation of the system, the total signal threshold is set just above noise level while the doublet threshold is adjusted up and down monitoring the rates at which the total signal crosses each of the thresholds. This information can be used with a mathematical model of the system to adjust the threshold reference voltage of the total signal to a level which appropriately measures all cells.

Figure 6A:
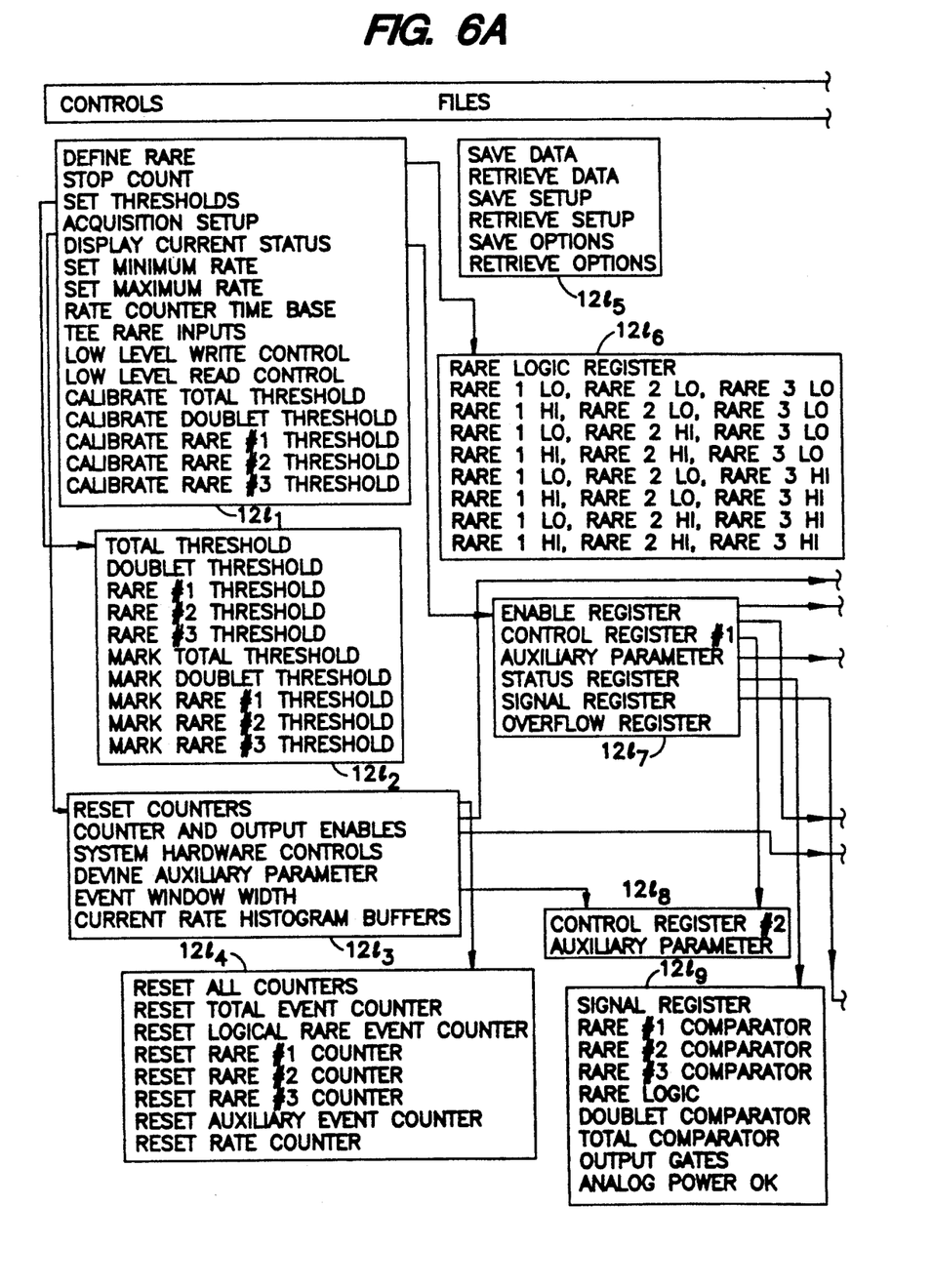
FIGS. 6A and 6B are schematic block diagram of software modules according to an embodiment or the invention.
Figure 6B:
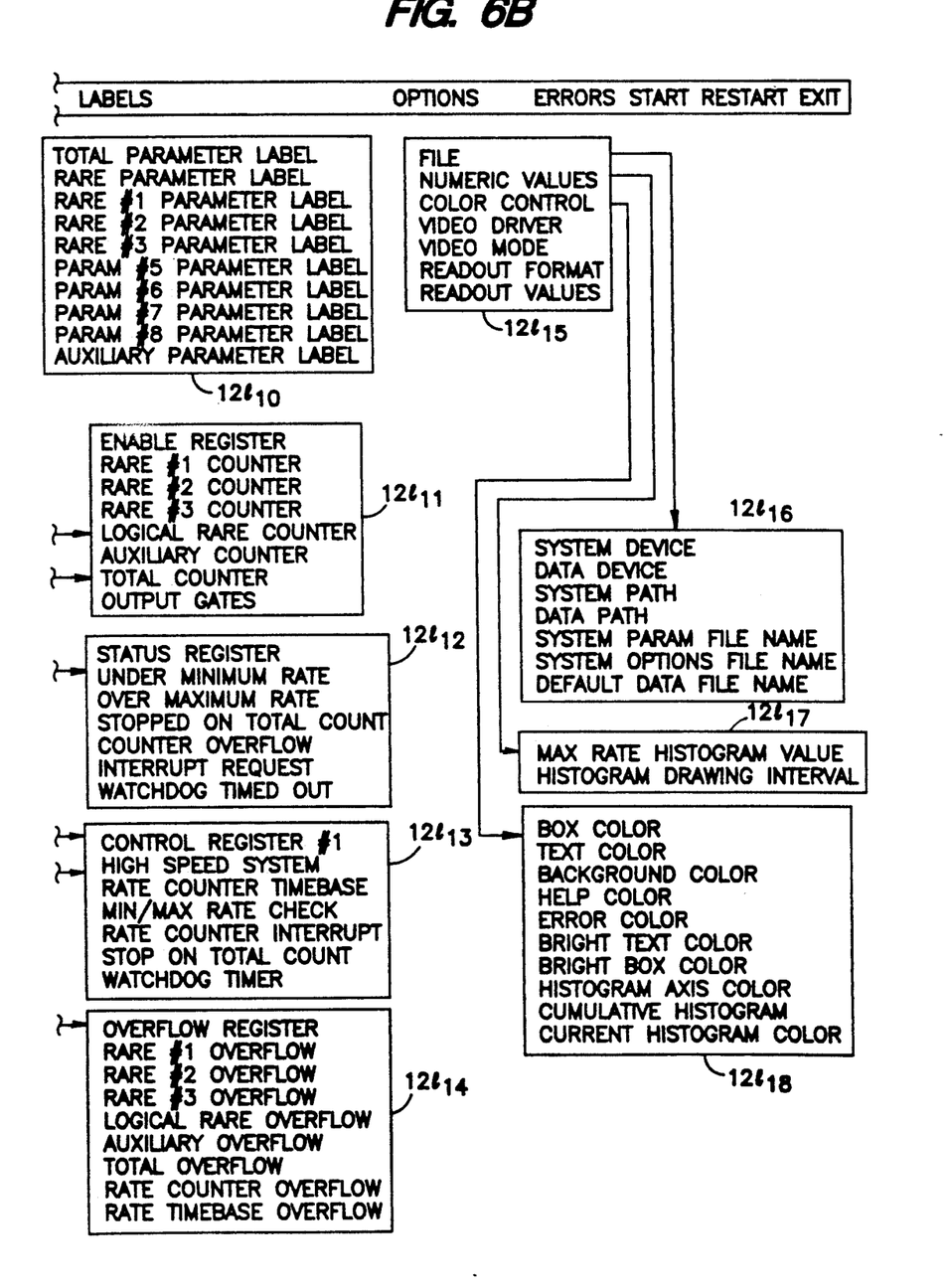

Referring to FIG. 6 for an overall block diagram of a software system, a menu driven user interface is provided to the particle sorting system. The software provides the operator with a flexible, menu-driven (with or without mouse support) interface to the present invention hardware circuitry while at the same time providing precise control over the process of data acceptance. In this implementation, the software is written in Borland Turbo C. The menu portion of the screen consists of pull-down menus and an area to allow system prompts and other messages to be displayed while the count and/or percent rare data are continually updated and the operator can manually stop the data acquisition to the system 12 at any time.

In this implementation, a control menu $12l_1$ lists examples of menu items which can be selected for system initialization. The "define rare" option of menu $12l_1$ calls cascading menu $12l_6$ for displaying values to be used in determining a rare condition in the gating logic $12h$. In menu $12l_1$ the "set thresholds" option calls menu $12l_2$ to allow the user to set values of the reference source voltages $12c$ which are compared to input detection signals in the comparators $12b$. In this L. implementation, the control menu $12l_1$ is also used for setting the minimum and maximum sorting rates, setting values for the rare inputs, currently implemented with "TEE inputs" which allows use of upper and lower limits on a single rare parameter in determining a rare condition, and for setting a counter time base value.

The software system also produces "rate histograms", (e.g. cumulative and within a user-defined current buffer) for the TOTAL events. The graphical capabilities of the program allow the operator to view these histograms continuously. The software system can also save to disk rate histograms, counter values and setup files for later analysis.

Figure 7:
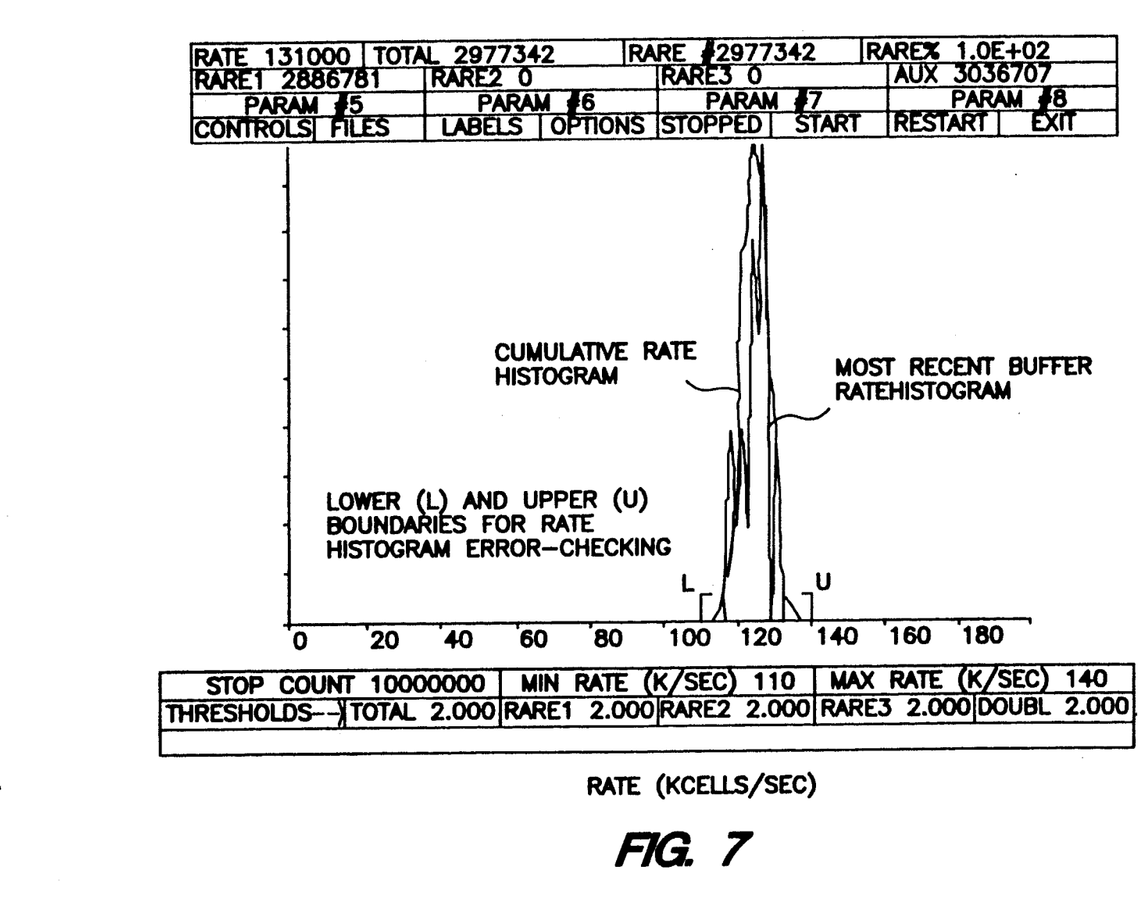
FIG. 7 illustrates a typical rate histogram produced by the invented particle sorting system.

FIG. 7 illustrates display of the parameters on the computer monitor a typical rate histogram for an example of a high-speed experiment displayed on the computer system. Rate histograms are used to diagnose flow problems as well as to provide important control data for high-speed runs. The histograms also provide a method for high-speed monitoring of flow problems which can lead to invalid data. In this implementation, the command of "acquisition setup" in menus $12l_3$, $12l_4$, $12l_8$, $12l_{11}$ and $12l_{13}$ initializes the system, resets counter registers $12f$ and enables counter registers $12f$ to begin counting. The acquisition setup also controls the system hardware and an auxiliary parameter used in calculating the total signal, as discussed above.

In this implementation, menu $12l_{15}$ is used to interface options for display of the information on a display monitor. Menu $12l_{18}$ is is cascaded from $12l_{15}$ for choices of display options for colors of the background of the display, menu boxes and histograms. The option of "numeric values" in menu $12l_{15}$ calls values of the rate at which the histogram is updated, menu $12l_{17}$. The parameters are initialized with menu $12l_{10}$ for labelling boxes on the screen display.

As illustrated in FIG. 6, menu $12l_5$ is an interface of software modules for saving options which were defined with the control menu $12l_1$, the hardware options menu $12l_{15}$ and the data accumulated in histograms during operation of the system. At the menu level, current counts and rate histograms may be separately viewed, saved or purged; the system may be configured or reconfigured, if so desired, using saved setup files.

The counter registers of the invention circuitry are polled on interrupts issued by the hardware. At operator-selected intervals a mean rate of flow is calculated and checked against operator-defined "rate windows" by the hardware. If a flow rate limit (window boundary) is exceeded, signal throughput is automatically halted, and the operator is immediately alerted. Optionally, the attached acquisition and fluidic systems may be shut down by this invention.

It will also be appreciated that various modifications, alternate constructions and equivalents may be employed without departing from the spirit and scope of the invention and that, therefore, the above description and illustration should not be construed as limiting the scope of the invention, which is defined by the appended claims.

We claim:

1. A particle sorter for counting and sorting a plurality of detection signals of a particle detector comprising:

a source of detection signals for respective particle parameters;

reference voltage means for developing a plurality of reference voltages;

comparator means for comparing each of said detection signals with a respective one of said reference voltages;

said comparator means generating a respective compared pulse when a detection signal exceeds a respective reference voltage;

counting means each actuated by compared pulses for a respective particle parameter for counting said compared pulses;

delay means for delaying said detection signals by a predetermined delay interval to thereby generate delayed detection signals;

logic means receiving said respective compared pulse signals and producing a logic signal whenever a selected combination of said respective compared pulses occurs during said predetermined delay interval;

gate means responsive to said logic signal for selectively allowing said delayed detection signals to pass through said gate means in response to said logic signal and for preventing said delayed detection signals from passing through said gate means in the absence of said logic signal.

2. A particle sorter as in claim 1 in which said logic means comprises logic timing means for determining said predetermined delay interval in response to one of said compared pulses and gate timing means for applying said logic signal to said gate means at a predetermined time.

3. A particle sorter as in claim 2 further comprising latching means coupled to said comparator means and said logic means for receiving said compared pulses and latching said compared pulses.

4. A particle sorter as in claim 3 further comprising a logic latching means coupled to said logic means, said logic timing means and said gate timing means for receiving said logic signal and latching said logic signal upon receiving a clocking and reset signal from said logic timing means at the end of said predetermined delay interval and resetting said latching means in response to said clocking and reset signal from said logic timing means.

5. A particle sorter of claim 4 further comprising output means coupled to said gate means for buffering said delayed detection signals which pass through said gate means.

6. A particle sorter of claim 5 further comprising input means coupled to said source of detection signals, said comparator means and said delay means for buffering and applying said detection signals to said comparator means and said delay means.

7. A method for sorting particles comprising:

applying a plurality of detection signals from a plurality of particle detectors to a delay circuit and respective comparators, said delay circuit effecting in said detection signals a predetermined delay in time and thereby producing delayed input signals;

comparing in said comparators the respective detection signals with respective thresholds producing respective compared pulse signals when respective detection signals meet respective thresholds;

determining a logic condition within said predetermined delay in time in response to said compared pulse signals and thereby producing a gate control signal;

gating said delayed input signals to an output means in response to said gate control signal.

8. A method as in claim 7 further comprising a step of applying said compared pulse signals to a count means for counting said compared pulse signals for the respective detection signals.

9. A particle sorter for sorting a plurality of detection signals of a particle detector comprising:

a reference voltage generator for generating a plurality of reference voltages of predetermined values;

a plurality of comparators each comparing a respective detection signal with a respective reference voltage and producing a respective compared pulse signal when a detection signal has a defined relationship with the reference voltage;

a delay circuit responsive to said plurality of detection signals for effecting in said detection signals a pre-determined delay in time to thereby generate delayed detection signals;

a logic control circuit connected to receive said compared pulse signals within a selected time window and to compare said received compared pulse signals to a logic condition and to produce a logic control signal whenever said compared pulse signals meet said logic condition; and a plurality of gates connected to receive said delayed detection signals and to receive said logic control signal and to open in response to said logic control signal, passing said delayed detection signals through said gates and to stay closed when said logic control signal is absent.

10. A particle sorter as in claim 9 further comprising a plurality of pulse counters associated with said plurality of comparators and each of said plurality of counters responsive to one of said comparators for counting a number of compared pulses.

11. A particle sorter as in claim 10 in which said logic circuit comprises a logic timing circuit for determining said predetermined delay in time in response to one of said compared pulses and a gate timing circuit for receiving said logic signal and applying said logic signal to said gate means at a predetermined time.

12. A particle sorter as in claim 11 in which said logic timing circuit generates a latch and reset signal at the end of said predetermined delay in time.

13. A particle sorter as in claim 12 further comprising a plurality of first latches, each of said plurality of first latches coupled to one of said plurality of comparators for latching one of said compared pulse signals and a second latch coupled to said logic control circuit for latching said logic control signal, said plurality of first latches being reset and said second latch being latched in response to said latch and reset signal.

14. A particle sorter as in claim 13 further comprising a plurality of output buffers coupled to said plurality of gates for receiving said delayed detection signals and for buffering said delayed detection signals.

15. A particle sorter as in claim 14 further comprising input buffers coupled to said plurality of detection signals, said plurality of comparators and said delay circuit for buffering said plurality of detection signals and for applying said plurality of detection signals to said plurality of comparators and to said delay circuit.

16. A particle sorter of claim 15 further comprising a logic condition counter, associated with said logic control circuit, responsive to said logic control signal for counting the logic control signal.

17. A particle sorter as in claim 16 further Comprising a data acquisition system coupled to said output buffers for processing said delayed detection signals.

18. A particle sorter for counting and sorting particles comprising:
- a first particle detector generating a plurality of detection signals of said first particle detector;
- a second particle detector generating a plurality of detection signals of said second particle detector;
- reference voltage means for developing a plurality of reference voltages of predetermined values;
- comparator means for comparing each of said detection signals of said first particle detector with a respective one of said plurality of reference voltages;
- said comparator means generating respective compared pulses when said each of said detection signals of said first particle detector is at least as great as said respective one of said plurality of reference voltages during a predetermined delay in time;
- a plurality of counting means each actuated by one of said respective compared pulses for counting said compared pulses;
- logic means receiving said respective compared pulses and producing a logic signal whenever one or more of said respective compared pulses occurs during said predetermined delay interval;
- gate means responsive to said logic signal for selectively allowing said detection signals of said second particle detector to pass through said gate means in response to said logic signal and for preventing said detection signals of said second particle detector from passing through said gate means in the absence of said logic signal.

19. A particle sorter as in claim 17 further comprising a pulse generating means coupled to said plurality of gates for applying to said data acquisition system reference pulses having an amplitude equal to respective of said plurality of reference voltages and amplifying means coupled to said output buffers and said data acquisition system for receiving said plurality of reference voltages and amplifying said plurality of reference voltages to determine the amplitude of said plurality of reference voltages relative to said detection signals.

20. A particle sorter as in claim 19 in which said amplifying means comprises linear amplification circuitries.

21. A particle sorter as in claim 19 in which said amplifying means comprises non-linear amplification circuitries.

22. A particle sorter as in claim 19 in which one of said plurality of reference voltages comprises a doublet threshold voltage said particle sorter further comprising a doublet comparator for comparing said doublet threshold voltage to said total signal producing a doublet compared pulse when a total detection signal has a defined relationship with said doublet threshold voltage and a doublet pulse counter for measuring a coincident condition and for adjusting said reference voltage values in response to said doublet counter value.

* * * * *